United States Patent [19]
Bowen et al.

[11] Patent Number: 5,736,369
[45] Date of Patent: Apr. 7, 1998

[54] METHOD FOR PRODUCING TRANSGENIC CEREAL PLANTS

[75] Inventors: Benjamin A. Bowen, Des Moines; Keith Lowe, Johnston; Margit C. Ross; Gary A. Sandahl, both of West Des Moines; Dwight T. Tomes, Cumming; William J. Gordon-Kamm; David D. Songstad, both of Urbandale, all of Iowa

[73] Assignee: Pioneer Hi-Bred International, Inc., Des Moines, Iowa

[21] Appl. No.: 483,091

[22] Filed: Jun. 7, 1995

Related U.S. Application Data

[63] Continuation of Ser. No. 282,270, Jul. 29, 1994, abandoned.

[51] Int. Cl.$^6$ .................... C12N 15/00; C12N 15/05; A01H 4/00
[52] U.S. Cl. .................... 435/172.3; 435/172.1; 435/412; 435/424; 435/430; 47/58; 47/DIG. 1; 800/205; 800/DIG. 56
[58] Field of Search .................... 800/200, 205, 800/250, DIG. 56; 47/58; 435/172.3, 172.1, 240.4, 145, 149, 412, 424, 430

[56] References Cited

U.S. PATENT DOCUMENTS

| | | | |
|---|---|---|---|
| 5,096,174 | 3/1992 | Vandeventer et al. | 800/200 |
| 5,164,310 | 11/1992 | Smith et al. | 435/172.3 |
| 5,177,010 | 1/1993 | Goldman et al. | 435/172.3 |
| 5,304,719 | 4/1994 | Segebart | 800/200 |

FOREIGN PATENT DOCUMENTS

| | | |
|---|---|---|
| 290 395 | 11/1988 | European Pat. Off. . |
| 0 301 749 | 2/1989 | European Pat. Off. . |
| 331 083 | 9/1989 | European Pat. Off. . |
| 400 553 | 12/1990 | European Pat. Off. . |
| WO 92/20809 | 11/1992 | European Pat. Off. . |
| WO 95/06127 | 3/1995 | European Pat. Off. . |
| 40 13 099 A1 | 10/1991 | Germany . |

OTHER PUBLICATIONS

Hajela, Ravindra K. et al., "A Simple Transformation System Using Adventitious Shoot Multiplication of Juneberry", *HortScience*, vol. 28(4), Apr. 1993.

Bilang, Roland et al., "Transient Gene Expression in Vegetative Shoot Apical Meristems of Wheat After Ballistic Microtargeting", *The Plant Journal* 4(4) pp. 735–744 (1993).

Pérez-Vicente, R. et al., "Culture of Vegetative and Floral Meristems in Rye-grasses: Potential Targets for Microballistic Transformation", *J. Plant Physiol*, vol. 142, pp. 610–617 (1993).

Christou, Paul et al., "Prediction of Germ-line Transformation Events in Chimeric R.Transgenic Soybean Plantlets Using Tissue-specific Expression Patterns", *The Plant Journal* 2(3), pp. 283–290 (1992).

(List continued on next page.)

*Primary Examiner*—Gary Benzion
*Attorney, Agent, or Firm*—Foley & Lardner

[57] ABSTRACT

To obtain a transgenic cereal plant which is stably transformed, an exposed cereal meristem is subjected to biolistic bombardment in order to target non-differentiated meristem cells for transformation. Immature embryos at the early proembryo, mid proembryo, late proembryo, transitional or early coleoptilar stage are harvested for biolistic bombardment. The meristem tissue or cells fated to contribute to the meristem then are manipulated in order to enlarge transgenic sectors, either through selection and/or through effecting a proliferation from the tissue of shoots or multiple meristems per se. The shoot population thus obtained then is screened, by means of a nonlethal enrichment assay, to identify either chimeric sectors that will contribute to germline transmission, or non-sectored, L2 periclinal chimeras that will by definition transmit to progeny. Increased time in culture, under selection, enhances the prospects for sectoral-to-periclinal conversions, and also selects for L1-to-L2 conversions which, through a shift in position, ultimately contribute to the germline. Transgenic sectors also are stabilized during the step of tillering.

17 Claims, 2 Drawing Sheets

OTHER PUBLICATIONS

Zhong, H. et al., "In Vitro Manipulation of Corn Morphogenesis for Transformation", Third International Congress of Plant Molecular Biology, 6–11 (Oct. 1991) (Abstract).

Potrykus, Ingo et al., "Gene Transfer to Cereals: An Assessment", Bio/Technology, pp. 535–542 (Jun. 1990).

Christou, Paul et al., "Inheritance and Expression of Foreign Genes in Transgenic Soybean Plants", Proc. Natl. Acad. Sci. USA, vol. 86, pp. 7500–7504 (Oct. 1989).

Ulian, E. C. et al., "Transformation of Plants via The Shoot Apex", In Vitro Cellular & Developmental Biology, vol. 24, No. 9 (Sep. 1988).

Cao, Jun et al., "Transformation of Rice and Maize Using the Biolistic Process", Plant Gene Transfer, pp. 21–33 (1990).

Gordon–Kamm, W. J. et al., "Transformation of Maize Using Microprojectile Bombardment: An Update and Perspective", In Vitro Cell Dev. Biol., 27P:21–27 (Jan. 1991).

Fromm, M. et al., "Transient Expression and Stable Transformation of Maize Using Microprojectiles", Plant Molecular Biology 2, pp. 219–224 (1991).

Gould, J. et al., "Transformation of Zea mays L. Using Agrobacterium tumefaciens and the Shoot Apex", Plant Physiol. 95, 426–434 (1991).

Schläppi, M. et al., "Competence of Immature Maize Embryos for Agrobacterium–Mediated Gene Transfer", The Plant Cell, vol. 4, 7–16, (Jan. 1992).

Potrykus, Ingo, "Micro–targeting of Microprojectiles to Target Areas in the Micrometre Range", Nature, vol. 355, pp. 568–569 (Feb. 6, 1992).

McCabe, D. E. et al., "Transformation of Elite Cotton Cultivars via Particle Bombardment of Meristems", Bio/Technology, vol. 11 (May 1993).

Zhong, Heng et al., "In–vitro Morphogenesis of Corn (Zea mays L.)", Planta, 187:483–489 (1992).

Potrykus, I., "Gene Transfer to Plants: Assessment of Published Approaches and Results", Annu. Rev. Plant Physiol. Plant Mol. Biol. 1991, 42:205–225 (1991).

Fromm et al., "Inheritance and expression of chimeric genes in the progeny of transgenic maize plants", Bio/Technology 8: 833–839 (1990).

Poethig et al., "Cell Lineage Patterns in Maize Embryogenesis: A Clonal Analysis", Developmental Biology 117: 392–404 (1986).

Dawe and Freeling, "Clonal Analysis of the Cell Lineages in the Male Flower to Maize", Developmental Biology 142:233–245 (1990).

De Wolff, "Techniques for the Vegetative Propagation of Maize", Euphytica 20: 524–526 (1971).

McCabe et al. "Stable Transformation of Soybean (Glycine Max) By Particle Acceleration", Bio/Technology 6: 923–926 (1988).

Lusardi et al. "An Approach Towards Genetically Engineered Cell Fate Mapping In Maize . . . " The Plant Journal 5(4): 571–582 (1994).

Lowe et al., "Germline Transformation of Maize Following Manipulation of Chimeric Shoot Meristems", Bio/Technology 13: 677–682 (1995).

Ritala et al. "Fertile Transgenic Barley By Particle Bombardment of Immature Embryos", Plant Molecular Biology 24: 317–325 (1994).

Gambley et al. "Microprojectile Transformation of Sugarcane Meristems and Regeneration of Shoots Expressing B–Glucuronidase", Plant Cell Reports 12: 343–346 (1993).

METHOD FOR PRODUCING TRANSGENIC CEREAL PLANTS

This application is a continuing application that claims benefit under 35 USC §120 to application Ser. No. 08/282,270, filed Jul. 29, 1994 now abandoned, the contents of which are hereby incorporated by reference.

BACKGROUND OF THE INVENTION

The present invention relates to obtaining plants by a methodology that entails the biolistic bombardment of meristem tissue, at a very early stage of development, and the selective enhancement of transgenic sectors, toward genetic homogeneity, in cell layers that contribute to germline transmission.

Production of transgenic plants first became routine through the use of Agrobacterium, and the use of this vector with totipotent tissues has become the method of choice for many dicotyledonous species. While steady progress has been made in expanding the genotype and species range of this method, Agrobacterium-mediated transformation has not been widely utilized for monocotyledonous species, including cereals, and is likely in the near term to remain restricted to specific genotypes. Similarly, protoplast-based methods are not widely applicable for monocots.

The first reports which appeared on biolistics-mediated production of fertile, transgenic maize were restricted to a specific hybrid, A188 x B73. See Gordon-Kamm et al., *Plant Cell* 2: 603 (1990), and Fromm et al., *Bio/Technology* 8: 833 (1990). Since then the technique has been extended to many important monocot crops, including barley, wheat, rice and oats, and the useful range in maize has been expanded slowly to include a handful of genotypes, for example, the commonly used A188 x B73, H99, FR16 and Pa91 genotypes. This work generally has revolved around a common theme, which is the initiation of regenerable callus from the scutellum of the embryo. In particular, all the reports in this context have highlighted a prerequisite of initiating regenerable callus from the scutellum of the immature embryo, regardless of whether there is bombardment (i) of the scutellum just after embryo isolation, followed by selection of the callus grown from the scutellar cells, (ii) of freshly initiated callus after a short preculture of the scutellum or (iii) of long-term callus or cell suspension cultures.

Progress in expanding the callus-based approaches to new genotypes or species has occurred via adaptations of the basic method to accommodate differences in morphology and growth patterns that typify different forms of immature, embryo-derived callus, i.e., friable callus versus compact callus, also referred to as Type II and Type I, respectively. Genotype restrictions remain, however, because some germplasm does not produce an appropriate callus response.

With the advent of biolistics-mediated transformation, numerous groups have explored the possibility of using microprojectile-delivery methods with meristem tissues. It has remained "an open question," however, as to "whether integrative transformation in cells of the shoot apical meristem of [a] monocotyledonous species is [even] possible." Bilang et al., *Plant J.* 4: 735 (1993).

The literature is marked by speculation concerning barriers to transforming meristem target cells which may explain the lack of success in this area. It has been observed, for example, that cereal "shoot meristems are tiny (about 100 μm) and . . . biolistic particles hit large target areas at random," and that "meristematic cells may [have] molecular mechanisms which prevents [sic] integration of foreign DNA . . . " Potrykus, *Nature* 355: 568, 569 (1992). More generally, the fact that monocot plant species tend to display less developmental plasticity than dicot species has engendered an expectation that monocots are less amenable to stable transformation by biolistic and other techniques.

Given the lack of developmental plasticity in cereals, therefore, the historical focus of transformation efforts in these crops has been on callus derived from one of the few genotypes that produce Type I or Type II embryogenic callus. These transformation targets were subject to easy use because a large population of undetermined, proembryogenic cells could be selected. Accordingly, many research groups have taken advantage of this approach and have not pursued alternative target tissues. In particular, no one to date has reported germline transformation via meristem bombardment of maize, a key cereal crop. Lack of success in this regard has been ascribed to the rigid developmental fate of the cells composing the meristem.

SUMMARY OF THE INVENTION

It is therefore an object of the present invention to provide a methodology for the reproducible production of stably transformed cereal plants.

In accomplishing this object and others, there has been provided, in accordance with one aspect of the present invention, a method for producing transgenic cereal plants, e.g., maize, sorghum, wheat, barley, oat or rice plants, that will transmit introduced DNA to progeny, comprising the steps of (A) introducing foreign DNA into cells selected from the group consisting of (i) cells of a meristem that is not enclosed by sheathing leaves and (ii) cells fated to contribute to said meristem; then (B) inducing reorganization of said meristem to increase transgenic sector size, whereby the likelihood that a transgenic sector will contribute to germline transmission is increased; and thereafter (C) exposing said meristem to conditions under which it differentiates to form a plantlet, wherein said plantlet contains said transgenic sector or is homogeneously transformed by said foreign DNA, such that said plantlet can be grown into a transformed cereal plant that will transmit said foreign DNA to progeny.

The foreign DNA can be introduced into a plurality of meristems, at least some of which differentiate in step (C) to form a plurality of plantlets. The foreign DNA is introduced into a meristem that is not enclosed by sheathing leaves including meristems from early proembryo, mid proembryo, late proembryo, transitional and early coleoptilar stage embryos.

In one preferred embodiment, reorganization is effected through at least one manipulation selected from the group consisting of (i) imposition of a nonlethal selective pressure on the meristems, (ii) mechanically-induced meristem reorganization, and (iii) hormonally-induced shoot multiplication. In another preferred embodiment the conditions in step (C) are such that the meristems undergo maturation and plant differentiation to form shoot apices, and the method further comprises effecting reorganization of meristem tissue in the shoot apices to enlarge transformed sectors or to produce periclinal L2 chimeras. The reorganization in this regard can be effected, for example, by exposing the shoot apices to nonlethal selection pressure such that transformed cells have a competitive growth advantage over nontransformed cells in the shoot apices, and the proportion of transformed cells in the shoot apices is increased. In yet another preferred embodiment, the method further comprises a step before step (B), e.g., before step (A), of wounding the apical dome selectively. A method of the present invention also can comprise the further steps of (i) dissecting out an axillary bud from above the base of a leaf of a plantlet when a chimeric sector is observed in a substantial portion of the leaf, and then (ii) germinating the axillary bud into a whole plant or subjecting the axillary bud to shoot multiplication.

In yet another preferred embodiment, the transgenic sector of a plantlet is stabilized by inducing tillers. The apex of a transgenic plantlet is removed, the wounded plantlet is grown to induce formation of a plurality of tillers, and transgenic tillers then are selected from that plurality.

In accordance with another aspect of the present invention, a transgenic cereal plant is provided that (A) is the product of a method as described above, (B) transmits introduced DNA to progeny and (C) belongs to a cereal line that is recalcitrant to callus-based transformation. In a preferred embodiment, the transgenic cereal is a maize plant that is not produced by transformation of a genotype selected from the group consisting of A188, A188 x B73, H99, Pa91, FR16 and a genotype obtained from a cross involving any of the foregoing.

According to still another aspect of the present invention, a maize plant is provided that transmits introduced DNA to progeny and that has a pedigree including a line selected from the group consisting of PHT47, PHP02, PHV78, PHK05, PHW20, PHR62, PHN37, PHM10, PHV37, PHJ65, PHBW8, PHK29, PHJ33, PHP60, PHN73 and PHHV4.

Other objects, features and advantages of the present invention will become apparent from the following detailed description. It should be understood, however, that the detailed description and the specific examples, while indicating preferred embodiments of the invention, are given by way of illustration only. Indeed, various changes and modifications within the spirit and scope of the invention will become apparent to those skilled in the art from this detailed description.

DETAILED DESCRIPTION OF THE PREFERRED EMBODIMENTS

Figure 1A:
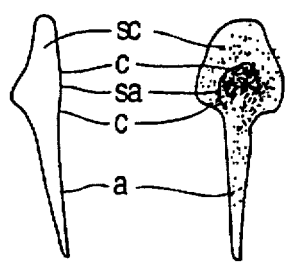
FIG. 1a–d is a series of line drawings depicting the structure of a typical cereal embryo (a) at the coleoptilar stage, which in maize occurs approximately 8 to 14 days after pollination, and (b) at the later third stage (about 22 to 28 days after pollination in maize), respectively; (c) the model shoot tip of an angiosperm, including cereals, shown in longitudinal section; and (d) the shoot and root structures which pertain in cereals generally, with a unit phytomer of the shoot highlighted. Abbreviations: c=coleoptile; cn=coleoptilar node; cp=coleoptilar pore; cr=coleorhiza; m=mesocotyl; r=primary root primordium; s=suspensor; sa=shoot apex; sc=scutellum; scn=scutellar node; sr=seminal root primordium.
Figure 1B:
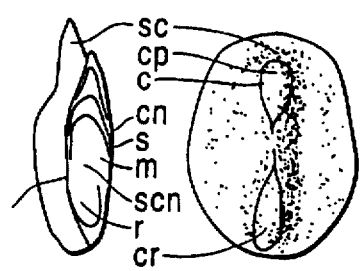
Figure 1C:
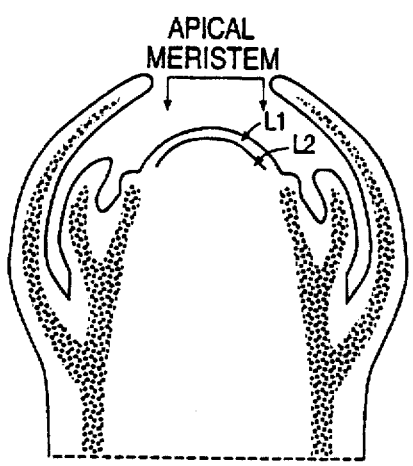
Figure 1D:
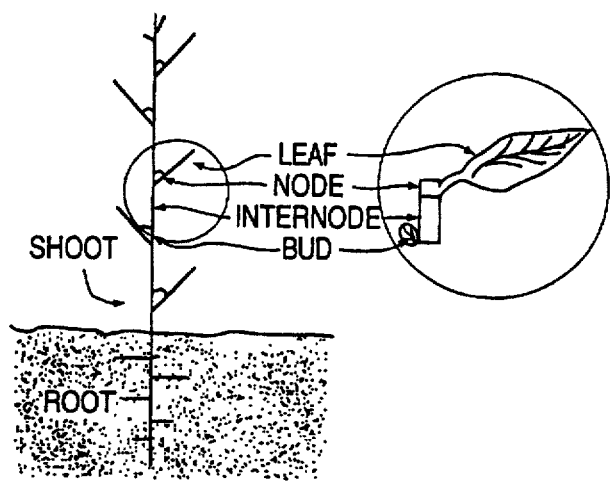

It has been discovered that the difficulties discerned previously in relation to applying a meristem-based transformation strategy to cereals can be overcome by (A) biolistically targeting cells of the shoot apical meristem under conditions such that the apical dome of the apical meristem is not enclosed by sheathing leaves, as depicted in FIG. 1; and (B) using a nonlethal selection regimen to effect an enrichment of transformed cells, for example, by giving transformed cells a competitive advantage over nontransformed cells, and thereby to facilitate an increase in sector width. The nonlethal selection also can promote the development of a short-lived, mericlinal L2 event into a stable, periclinal event in which most or all of the cells contributing to the germ line (i.e., the L2 layer) are transformed. In addition, it has been found that selective pressure can promote L1- to -L2 conversion events, thus increasing the probability of germ line transmission.

The shoot apical meristem in cereals is highly variable between species. In most species, however, a stratified meristem exists that is composed of two or three visible layers which generate the entire shoot: a superficial L1, a subsurface L2 and, in some cases, a deeper L3 layer. The outer layer(s) comprise the tunica, which are characterized by anticlinal cell divisions. In contrast, divisions in the innermost layer, the corpus, occur randomly, both anticlinally and periclinally. In maize the meristem is believed to be composed of only two layers, L1 and L2, and possibly a third L3 layer. See Poethig, CONTEMPORARY PROBLEMS IN PLANT ANATOMY 235–39 (1984). Cell differentiation to delimit the major tissues of the shoot is position-dependent rather than lineage-dependent.

For example, in most species the epidermis is generated almost exclusively by the L1 layer, with the L2 layer contributing to the germ line. In the process of introducing a foreign gene into a subset of apical meristem cells, one creates a plant that necessarily is "chimeric," i.e., a plant in which portions have been altered in genetic composition. There are three major categories of chimeric plants, based on the characteristic pattern of genetic differences: (1) sectoral chimeras, in which a portion of the plant is "genetically distinct" through all cell layers by virtue, for example, of displaying a mutant somatic phenotype, a change in chromosome number, or the presence of transformed cells; (2) periclinal chimeras, in which an entire cell layer (L1 alone or L2 alone, for instance) is different from the rest of the plant; and (3) mericlinal chimeras, which represent an intermediate between the other two types, i.e., a genetic difference characterizes only a portion of one layer.

In this description, the terms "biolistic" and "biolistically" denote an approach to genetic transformation described, for example, in U.S. Pat. Nos. 4,945,050 and 5,141,131, the respective contents of which are hereby incorporated by reference.

Pursuant to a biolistic approach, force is transmitted to small particles that carry DNA, for example, coated on particulate surfaces or absorbed into the particles, in such a way that the exerted pressure forces particles into a targeted cell or tissue ("biological sample"); the particles thus are called "microprojectiles" or "microcarriers." In other words, the microprojectiles are propelled at the biological sample, accelerating to such speed that, upon impact, they penetrate cellular surfaces and are incorporated into the interior of a cell or cells in the sample.

The microprojectiles should have an average diameter sufficiently small to permit penetration of and retention by cells of the biological sample without killing the cells. Particles of gold or tungsten, in the size range of about 0.1 to 4 microns, are illustrative of microprojectiles that are suitable for delivering exogenous nucleic acid into a host. Other types of biolistic delivery vehicles are disclosed, for example, by U.S. Pat. Nos. 5,120,657 (electrical discharge propels a carrier sheet toward target) and 5,240,842 (nucleic acid delivered via aerosol droplets), and in PCT application WO 92/01802 (ice particles as carrier).

In relation to aspect (A) mentioned above, the present invention contemplates the biolistic targeting of apical meristem cells at an early developmental stage. In a preferred embodiment, meristem cells are bombarded at a developmental phase that is no later than the coleoptile-ring stage, when the apical dome is fully exposed, lacking protection from leaf primordia, and is composed of fewer cells in the meristem than are present at later stages. The stages of maize embryogenesis are described in detail by Poethig et al., *Developmental Biology* 117: 392–404 (1986), the contents of which are incorporated by reference.

More specifically, the transformation method of the present invention focuses on coleoptilar and earlier stage embryos, namely, early proembryo, mid proembryo, late proembryo, and the transitional stages of embryo development. At the earliest stages of development, the meristem is not defined; instead, a group of cytoplasmically dense cells undergo more rapid division and, ultimately, form the apical meristem.

In targeting these various embryo stages, therefore, DNA is introduced (i) into cells that make up the meristem proper (i.e., at the coleoptilar stage) or, (ii) in the earlier stages of development, into cells that are destined, by position or fate, to contribute to the meristem. Biolistic bombardment according to the present invention is effected by orienting the embryo so that cells that are within a meristem or that are destined to contribute to the meristem are exposed directly to the biolistic projectiles.

In late proembryos, the axis side of the embryo is slightly flattened, allowing this side of the embryo to be placed face up (away from the agar) for bombardment. Transition stage and coleoptilar stage embryos are similarly oriented. There is no such orientation, however, for mid and early proembryos on agar after isolation (i.e., before shooting). Rather, when proembryos are placed in a random orientation on the agar medium, the meristem apparently develops on the upper side of the embryo (away from the medium). Thus, placement on the medium may be stimulating the embryo to re-orient its growth axis, for example, by virtue of the in vitro conditions which are provided (i.e., the new hormonal gradient that is being established within the embryo).

A convenient and, hence, preferred source of meristems for use in the present invention are coleoptilar stage embryos. At the coleoptilar stage of cereal embryo development, the coleoptile is visible as a ring of leaf primordium surrounding an exposed meristem. In maize, the early coleoptilar stage can generally be obtained 10 to 12 days after pollination. (The days-after-pollination criterion, or "DAP," is affected by embryonic environment and genotype, and therefore is an adjunct to developmental staging based on morphology, which is an important criterion for timing of transformation in the present invention.) At the early coleoptilar stage the boundary of the meristem is distinct, with a visible tunica and corpus (L1 and L2 layers, respectively).

A particularly preferred source of target cells for use in the present invention are present in the early proembryo, mid proembryo, late proembryo and the transitional stages in embryo development. In maize, the early proembryo, mid proembryo, late proembryo and the transitional stages can generally be isolated 2, 4, 7–8 and 8–10 DAP, respectively (see Poethig et al. (1986), cited above). Again, the developmental stage is the important criterion. Rate of development and, hence, DAPs at which embryos are isolated vary with growth environment and genotype.

At the mid proembryo stage there is no distinction between the L1 and L2 layers. The distinction between L1 and L2 progresses until it is well-defined by the time the embryo reaches the transitional stage.

Alternatively, immature staminate inflorescences (tassels) and pistillate inflorescences (ears) can serve as sources of meristems for transformation in accordance with the present invention. "Immature" here denotes a developmental state when floral meristems still are developmentally plastic, i.e., are capable of shoot differentiation. This developmental plasticity should be exploitable, pursuant to the present invention, for transformation of many Graminaceous species, given the recognized similarities in inflorescence development among the grasses.

A trained technician can isolate 200 to 600 mid proembryo, late proembryo, transitional or coleoptilar-stage embryos per day, the ease of isolation and number of isolated embryos increasing with embryo size. On the order of ten times as many meristem explants can be isolated from immature tassels and/or ears, and a large percentage of these can be induced to follow a vegetative pattern of development. Another important advantage associated with using floral explants as meristem sources is that many genotypes exhibit better meristem growth and shoot multiplication when the floral explants are the starting material. This advantage is pronounced, for example, with respect to an inbred maize line with a lineage that includes line PHV78. Conversely, immature embryos are the preferred explant for some genotypes, such as maize inbreds having a lineage including line PHBW8. Access to both options significantly extends the genotype range for meristem transformation pursuant to the invention.

Figure 2:
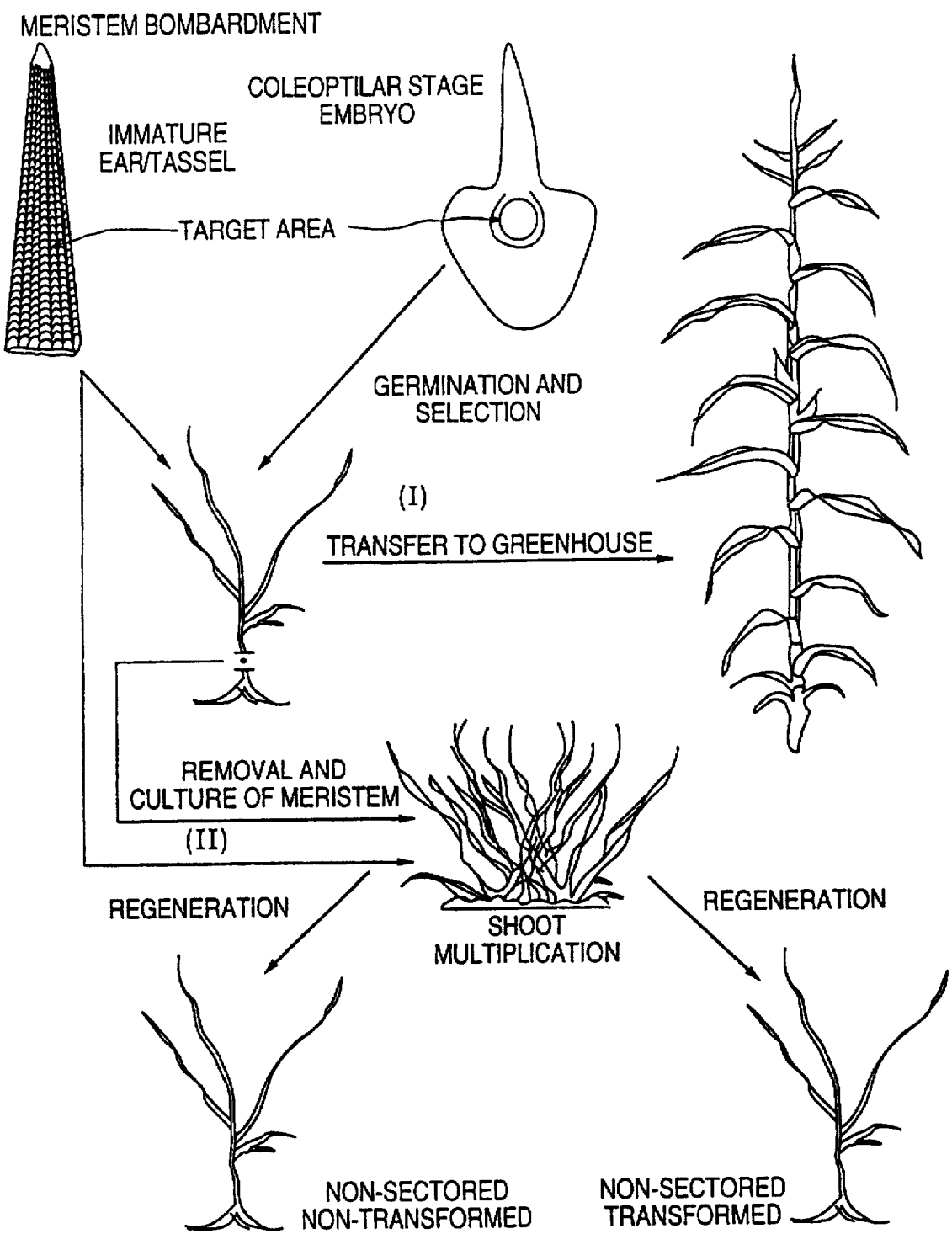
FIG. 2 is a schematic representation of transformation methodology according to the present invention.

Whatever explant or tissue is used as a source of target cells for biolistic treatment in accordance with the present invention, the bombarded cells are subjected to a first, nonlethal selection pressure in the course of generating plantlets which are grown out directly (course I in FIG. 2) or, alternatively, are subjected to meristem reorganization, induced mechanically or hormonally, in advance of a second nonlethal selection (course II in FIG. 2). The aspects of nonlethal selection and induced meristem reorganization are addressed in greater detail below.

The developmental fate of cells within the meristem normally is rigidly determined. Thus, transformation of a particular cell within the meristem typically will result in a small transgenic sector made up only of the descendants of that cell. Without further manipulation, such sectors rarely if ever overlap gametophytic tissue during normal development. But by targeting cells at earlier developmental stages, as described above, and then applying mild selective conditions in accordance with the present invention, i.e., the pressure provides a growth advantage to transformed cells but is not severe enough to impede the overall development of the meristem, then the consequent faster division rate of transformed cells results in the descendent cells comprising a greater portion of the meristem. Accordingly, the transgenic sector contributes to a larger portion of the mature plant, and there is a greater likelihood that the sector will contribute to germline transmission.

According to one preferred embodiment, a selective growth advantage is imparted to transformed cells in the form of NPTII-encoded resistance to tobramycin, kanamycin or a related compound. It is acceptable, however, to confer resistance to another "bleaching" antibiotic (by means of a streptomycin-resistance gene, for instance) or herbicide, for example, by transformation with the crtI gene, which imparts resistance to norflurazon. By the same token, the present invention contemplates similar non-lethal strategies which entail the use of other selective agents, such as bialaphos and hygromycin, with a corresponding, resistance-imparting gene, so long as the resulting selective pressure retards the growth of non-transformed cells relative to cells in the transgenic sector.

A model experiment in this regard would involve exposing samples of isolated meristem tissue to a graded series of dilutions of the selection agent in the medium of choice, and then determining a concentration threshold below which the selective pressure favoring transformed cells is not so stringent as to be detrimental to general meristem development. While this approach typically would result in continued meristem growth during selection, the present invention also envisages establishing conditions of little or no meristem growth ("static conditions") which are punctuated by brief exposure(s) to a higher concentration of selection agent ("pulsed selection") which otherwise would adversely affect overall meristem development.

As noted above, cereal transformation according to the present invention optionally involves a reorganization of the meristem, for example, by wounding of the apical dome. While other methods of wounding also result in reorganization, a preferred method is to pierce the apical dome using a micromanipulation needle. The reorganization thus effected alters growth in the apical dome and, it has been discovered, prompts a proliferation of multiple meristems which, in turn, enhances transformation frequency and sector size. For example, mechanically-induced meristem proliferation in conjunction with selective pressure results in an increase in frequency and size of the transgenic sectors observed in subsequent leaves.

Meristem reorganization may precede biolistic treatment, followed by germination and selection leading to the production of chimerically transformed plants (course I). Alternatively, mechanical wounding can be performed after bombardment of the meristems in order to effect a proliferation of meristems. When applied in this manner on chimeric meristems, the sectors can enlarge because the reorganized meristems are derived from a smaller number of cells and, hence, the percentage of transformed cells in the meristems is increased.

Pursuant to course II (see FIG. 2), a reorganization is brought about by hormonally-induced shoot multiplication with respect to the developing shoot meristem of a plantlet selected for the presence of a transformed sector. The hormonally induced reorganization need not be exclusive of the optional, mechanically induced reorganization mentioned above, and brings about meristem proliferation via shoot multiplication.

To effect hormonally induced reorganization, the developing shoot meristem first is localized, typically in a swelling that occurs in the germinated plantlet at the junction between the mesocotyl and the epicotyl (see FIG. 2). A section of 2 to 3 mm in size which contains the meristem then can be excised at the swelling point and cultured on a shoot proliferation medium of the sort described, for example, by Lowe et al., Plant Science 41: 125 (1985), and by Zhong et al., Planta 187: 483 (1992), respectively. To this end, meristems typically are cultured on MS medium with 2 mg/l BAP (6-benzyl-aminopurine), 3% sucrose and 9 mg/l agar. More generally, a shoot multiplication medium will utilize a cytokinin, such as Kinetin, BAP, Thidiazuron or Zeatin, at a concentration between 0.5 and 10 mg/l. A low level of auxin also may be required in some genotypes. Murashige and Skooge (MS) salts are adequate but probably not optimal, in that preliminary experiments using media with ammonium levels higher than those in MS resulted in an improved culture response. Additional additives such as the auxin transport inhibitor, TIBA, and ethylene inhibitors like silver nitrate and cefotaxime also appear to be beneficial.

By virtue of its hormonal constituency, the shoot proliferation medium forces the generation of a few to hundreds of shoots from each excised shoot meristem, thereby increasing the likelihood of obtaining a subpopulation of shoots, some of which may arise from a transformed sector. Unlike mericlinal and sectoral chimeras, which exhibit a lower probability of germline transmission, a significant and reproducible percentage of the resulting shoots are periclinal chimeras and, hence, are "stabilized" in the sense that genetic homogeneity is promoted within a cell layer, such as the L2 layer, that ultimately contributes to germline transmission.

To identify the aforementioned shoot subpopulation, the large population of induced shoots is screened to identify non-sectored, periclinal chimeras. This is accomplished via a nonlethal assay which brings about an enrichment of transformed cells through the use of selective agents (i) that bleach normally green tissue at levels that do not inhibit growth or (ii) that inhibit growth of non-transformed meristem sectors without significantly reducing viability of the meristems.

Use of an appropriate selective agent at nonlethal levels, as described, also provides the opportunity to assess visually the extent of homogeneity within a transformed meristem layer. Increased time in culture under selection, pursuant to the present invention, enhances the prospect of mericlinal-to-periclinal conversions and of sectoral-to-homogeneously transformed conversions, and also selects for L1-to-L2 conversions which, through a shift in position, ultimately contribute to the germline.

From the preceding commentary it is apparent that one aspect of the present invention relates to forcing meristem reorganization, before bombardment, after bombardment or both, by suppressing cell growth through selective wounding of the apical dome, prompting generation of multiple meristems, or by exposing excised meristems to hormonal stimuli likewise leading to multiple meristems, albeit in the form of proliferated shoots. According to yet another preferred embodiment, the axillary bud of a transformed plantlet can be dissected out, from just above a leaf base, when a chimeric sector is observed in a substantial portion of that leaf. The isolated axillary bud represents an additional meristem that can be grown into a whole plant, or taken through a brief cycle of shoot multiplication as described, thereby to obtain a more homogeneously transformed plant.

The purpose of this approach, as for the others discussed above, is to increase the frequency of germline transmission. Thus, if a transformed sector runs through more than one leaf, it should be possible to "capture" that transformation event in a axillary bud, i.e., convert a transformed mericlinal or sectoral chimera into a periclinally or homogeneously transformed shoot.

Another method of stabilizing transgenic sectors is to induce tillers in the transformed plant. In those cases in which transgenic sectors are limited to the lowermost leaves or domains of maize plants, tillering is induced to stabilize these transgenic sectors.

By means of the present invention, a wide range of cereal varieties can be transformed stably, in a genotype-independent manner, for the first time. In maize, for example, this means that elite lines which were previously inaccessible to transformation characterized by transmission of imparted trait(s) to seed progeny now can be genetically engineered to express various phenotypes of agronomic interest. The genes implicated in this regard include but are not limited to those categorized below.

I. Genes That Confer Resistance To Pests or Disease And That Encode:

(A) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), under ATCC accession Nos. 40098, 67136, 31995 and 31998.

(B) A lectin. See, for example, the disclosure by Van Damme et al., *Plant Molec. Biol.* 24: 825 (1994), who disclose the nucleotide sequences of several *Clivia miniata* mannose-binding lectin genes.

(C) A vitamin-binding protein such as avidin. See U.S. patent application Ser. No. 07/911,864, the contents of which are hereby incorporated by reference. The application teaches the use of avidin and avidin homologues as larvicides against insect pests.

(D) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* α-amylase inhibitor).

(E) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(F) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(G) An insect-specific venom produced in nature by a snake, a wasp, etc. For example, see Pang et al., Gene 116: 165 (1992), for disclosure of heterologous expression in plants of a gene coding for a scorpion insectotoxic peptide.

(H) An enzyme responsible for an hyperaccumulation of a monterpene, a sesquiterpene, asteroid, hydroxamic acid, a phenylpropanoid derivative or another nonprotein molecule with insecticidal activity.

(I) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(J) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(K) A hydrophobic moment peptide. See U.S. patent applications Ser. No. 08/168,809 (disclosure of peptide derivatives of Tachyplesin which inhibit fungal plant pathogens) and serial No. 08/179,632 (teaches synthetic antimicrobial peptides that confer disease resistance), the respective contents of which are hereby incorporated by reference.

(L) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(M) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(N) An insect-specific antibody or an immunotoxin derived therefrom. Thus, an antibody targeted to a critical metabolic function in the insect gut would inactivate an affected enzyme, killing the insect. Cf. Taylor et al., Abstract #497, *SEVENTH INT'L SYMPOSIUM ON MOLECULAR PLANT-MICROBE INTERACTIONS* (1994) (enzymatic inactivation in transgenic tobacco via production of single-chain antibody fragments).

(O) A virus-specific antibody. See, for example, Tavladoraki et al., Nature 366: 469 (1993), who show that transgenic plants expressing recombinant antibody genes are protected from virus attack.

(P) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D- galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(Q) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

II. Genes That Confer Resistance To A Herbicide, For Example:

(A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively.

(B) Glyphosate (resistance imparted by mutant EPSP synthase and aroA genes, respectively) and other phosphono compounds such as glufosinate (PAT and bar genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+genes) and a benzonitrile (nitrilase gene). Przibilla et al., *Plant Cell* 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC accession Nos. 53435, 67441 and 67442. Cloning and expression of DNA coding for a glutathione S-transferase is described by Hayes et al., *Biochem. J.* 285: 173 (1992).

III. Genes That Confer Or Contribute To A Value-Added Trait, Such As:

(A) Nutritional enhancement, as illustrated by (1) Higher lysine content: A cereal such as maize could be transformed with a gene that increases lysine content, making the cereal nutritionally more complete and thereby eliminating need for added lysine, for example, in poultry and swine feeds.

(2) Higher methionine content: A gene would be added to increase methionine levels in a cereal crop to offset an overall low methionine content, for example, in a poultry feed which combines lower- and higher-methionine components such as soybean and maize, respectively.

(B) Decreased phytate content (1) Introduction of a phytase-encoding gene would enhance breakdown of phytate, adding more free phosphate to the transformed cereal. For example, see Van Hartingsveldt et al., Gene 127: 87 (1993), for a disclosure of the nucleotide sequence of an *Aspergillus niger* phytase gene.

(2) A gene could be introduced that reduces phytate content. This could be accomplished, for example, by cloning and then re-introducing DNA associated with the single allele which is responsible for maize mutants characterized by low levels of phytic acid. See Raboy et al., *Maydica* 35: 383 (1990).

(C) Modified carbohydrate composition effected, for example, by transforming maize with a gene coding for an enzyme that alters the branching pattern of starch. See Shiroza et al., *J. Bacteriol.* 170: 810 (1988) (nucleotide sequence of Streptococcus mutans fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* α-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley amylase gene), and Fisher et al., *Plant Physiol.* 102: 1045 (1993) (maize endosperm starch branching enzyme II).

Synthesis of genes suitably employed in the present invention can be effected by means of mutually priming, long oligonucleotides. See, for example, Ausubel et al. (eds.), CURRENT PROTOCOLS IN MOLECULAR BIOLOGY, pages 8.2.8 to 8.2.13 (Wiley Interscience 1990), and Wosnick et al., Gene 60: 115 (1987). Moreover, current techniques which employ the polymerase chain reaction permit the synthesis of genes as large as 1.8 kilobases in length. See Adang et al., *Plant Molec. Biol.* 21: 1131 (1993), and Bambot et al., *PCR Methods and Applications* 2: 266 (1993).

Maize lines that can be transformed via the present invention include, among others, inbreds that are employed in producing commercial hybrids. These inbreds, both proprietary and publicly-available, span many heterotic families. The preferred representatives within the heterotic groupings, and the relative use of entire heterotic patterns, vary with the market in question. For example, different germplasm is favored when breeding for the continental United States, including different geographic areas of adaptation (for example, the South, the East, the West, the North and the Central Corn Belt), for Europe and for South America, as well as for other international markets.

Callus-mediated methodology is unsuitable for many inbreds which do not produce the required callus response or which provide callus that grows in a manner rendering the methodology unusably inefficient ("recalcitrant" inbreds). Accordingly, such methodology has been limited to a large extent to transformation of a few genotypes, such as, in maize, A188, A188 x B73, H99, Pa91, FR16 and genotypes obtained via a cross involving one of these genotypes. By contrast, meristem transformation pursuant to the present invention is applicable to any line, regardless of how that line responds to callus-mediated transformation. Thus, even cereal lines heretofore deemed recalcitrant to transformation can be transformed stably via the present invention. Illustrative of the maize inbreds thus affected are PHT47, PHP02, PHV78, PHK05, PHW20, PHR62, PHN37, PHM10, PHV37, PHJ65, PHBW8, PHK29, PHJ33, PHP60, PHN73, and PHHV4. By the same token, the present invention should be applicable to newly-developed inbreds and to new heterotic groups which are created through the combination of existing germplasm, including "exotic" material brought into breeding programs from sources in the tropics and elsewhere.

According to a preferred embodiment, therefore, the present invention contemplates a transgenic plant that belongs to a cereal line that is recalcitrant to callus-based method transformation. Conversely, another preferred embodiment encompasses transgenic maize plants that are not produced by transformation of A188, A188 x B73, H99, Pa91 or FR16. In this context, the phrase "cereal line" denotes a group of gramineous plants of the sub-family Poaoideae which display relatively little variation between individuals with respect to more than one distinctive trait, generally although not exclusively by virtue of several generations of self-pollination. (In addition, the term "line" here is used sufficiently broadly to include a group of plants vegetatively propagated from a single parent plant, via tissue culture techniques.) A plant is said to "belong" to a particular line if it (A) is a primary transformant ($T_0$) plant regenerated from material of that line or (B) has a pedigree comprised of a $T_0$ plant of that line. In this context, the term "pedigree" denotes the lineage of a plant, e.g., in terms of the sexual crosses effected such that a gene or a combination of genes, in heterozygous (hemizygous) or homozygous condition, imparts a desired trait to the plant.

The present invention is further described in the following examples, which are illustrative only. In carrying out the examples, a general procedure was followed for biolistic transformation. According to this procedure, 60 mg of 1.0 to 1.8 μm tungsten microprojectiles (source: General Electric) were suspended in 2 ml of 0.1M $HNO_3$ and sonicated for twenty minutes on ice. After centrifugation at 10,000 rpm to remove $HNO_3$, 1 ml of sterile deionized water was added, followed by a brief sonication and further centrifugation. This water rinse was repeated twice, after which the water was removed and 1 ml of 100% EtOH was added. The particles were resuspended by sonication, and the EtOH rinse was repeated. After the addition of 1 ml of sterile, deionized water and a further sonication, four aliquotes of the resulting suspension (250 μl each) were pipetted into separate tubes (2 ml volume). Sterile, deionized water (750 μl) was added to each tube, which then could be stored at –20° C. For purposes of DNA preparation, 50 μl of the sonicated tungsten microprojectile suspension were pipetted into a 1.5 ml tube, to which was added 1 to 10 μg of the foreign DNA. After mixing, 50 μl of 2.5 M $CaCl_2$ solution were added and, with further mixing, 20 μl of 0.1 M spermidine also were introduced. The resulting composition was mixed, sonicated, and then centrifuged for about ten seconds. After the supernatant was withdrawn and 250 μl of 100% EtOH were added, the composition again was sonicated and centrifuged, and the supernatant was withdrawn. Finally, 30 μl of 100% EtOH solution were added to the composition, which thereafter was used, in a 5 μl aliquot per shot, with rupture disks ranging from 200–1100 p.s.i.

EXAMPLE 1

Transformation with Non-Lethal Selection
(A) Evaluation of Maize Histone Promoter Linked to NPTII Ears of a proprietary maize genotype, designated "N10000" for purposes of this description, were harvested seven days after pollination at the early coleoptilar stage of development. Harvested ears were surface-sterilized in 50% Chlorox with Tween 20 for 20 minutes, and then rinsed three times with sterile deionized water. Kernel tops were removed with a scalpel and embryos were dissected from endosperm. Sixty-seven embryos were placed axis side up, 10 embryos per plate, onto maturation medium (MS salts, 0.1 g/L myoinositol, MS vitamins, 0.5 mg/L zeatin, 150 g/L sucrose, and 6 g/L Sea-Kem agarose; pH 5.6 prior to autoclaving). Embryos were incubated overnight at 28° C. in the dark before bombardment.

In these studies, embryos were transformed with plasmids DP6212 and DP3953. DP6212 contains the 2xhistone-143 promoter, the first intron of the maize ADH1 gene, the nptII gene encoding neomycin phosphotransferase (NPTII), and a 3' transcript processing region from the Proteinase Inhibitor II (PinII) gene of potato. DP3953 contains the ubiquitin promoter, the first intron of the ubi gene, the gene encoding β-glucuronidase (GUS), and a 3' transcript processing region from the PinII gene. Embryos were bombarded with DP6212 and DP3953, mixed at a 1:1 ratio, at a concentration of one 1 μg of total DNA per tube of acid-washed tungsten particles. This concentration, at ten times less than the standard, was optimal for yielding transformants with more uniform GUS staining patterns and yet having no detrimental effect on the function of the selectable marker or the frequency of transformation.

Pursuant to the above-discussed biolistics protocol, the particles were delivered as five 5-μl shots per tungsten tube, using a PDS-1000 Helium gun with 1100 p.s.i. rupture disks. All embryos received one bombardment per plate.

After bombardment, embryos were maintained at 28° C. in the dark for seven days on Maturation Medium. Embryos then were transferred to 272K shoot elongation medium (MS salts, 0.1 g/L myoinositol, MS vitamins, 30 g/L sucrose, and 4 g/L gelrite) which contained 150 mg/L tobramycin sulfate as the selection agent. Embryos were incubated in the light at 28° C. At the time of transfer, embryos had elongated cotyledons.

At two, three and four weeks after bombardment, recovered plantlets were sampled and analyzed for GUS expression via methodology described by McCabe et al., *Bio/Technology* 87: 923-26 (1988). Leaf tips were placed in about 200 μl of histochemical stain and allowed to incubate at 37° C. overnight in the dark to maximize GUS expression. Data from the first and second leaves are summarized in the following table.

TABLE 1

| GUS Activity in Tissues of Transformed N10000 | | | |
|---|---|---|---|
| Plate | #Plants Analyzed | #GUS + | GUS Sector Type |
| 1 | 9 | 6 | half leaves |
| 2 | 8 | 5 | half leaves or spotty |
| 3 | 9 | 4 | linear sectors |
| 4 | 9 | 6 | half leaves or spotty |
| 5 | 7 | 3 | linear sectors |
| 6 | 11 | 2 | complete staining |

Any plantlets showing positive sectors were transferred to culture tubes containing shoot elongation medium that did not contain tobramycin. Each new leaf was examined for GUS expression. Plantlets that were consistently positive for GUS were transferred to the greenhouse for maturation when root development was well established. Plants that stopped expressing GUS were observed for phenotype changes, i.e., necrosis, bleaching or general lack of growth, which indicated that an escape from selection had occurred.

Plants with normal phenotypes were analyzed for NPTII protein by means of a NPTII ELISA kit available from 5'→3', Inc., 5603 Arapahoe Road, Boulder, Co. 80303 (catalog No. 5307-661-514). Positives were transferred to the greenhouse.

Transgenic plants maturing in the greenhouse were sampled for GUS activity or NPTII protein in each new leaf and in tassel and ear tissues to characterize the expression pattern in each plant. Pollinations were completed as selfs or as sibs. Eight to ten days after pollination, embryos were rescued by harvesting and surface sterilizing the ears, excising the embryos and placing the embryos on shoot elongation medium for germination. (This procedure was not required but was preformed to accelerate the analysis process.) T1 leaf tissue was sampled for GUS histochemical assays and painted with 2% kanamycin sulfate in 0.2% SDS buffer to verify transmission of the transgenes. Samples of mature leaves were harvested from the T0 transformant for Southern analysis to further characterize the transformation.

Histochemical analysis of one N10000 plant, designated "2–4," demonstrated that GUS was expressed in leaves, silks (primary ear), primary ear husks and cob, and central spike and branches of tassel. In addition, Southern analysis confirmed the presence of the NPTII structural gene in leaf tissue harvested from the mature $R_0$ plant. Segregation of this hybridizing band correlated with NPTII-positive ELISA results in this plant. Analysis of the central stalk also showed GUS expression in epidermal layer of adventitious roots and in a vascular bundle of the central stalk.

(B) Transformation of Maize Lines with Non-Lethal Selection

Experiments were performed to determine the efficacy of non-lethal selection in a variety of maize genotypes. Genotype N10000 and several other proprietary genotypes, designated "P10000," "W20000," "E10000," "PHP02" and "R20000," respectively, for purposes of this description, were transformed with plasmids DP6212 and DP3953 as described above. Table 2 below enumerates data showing that the non-lethal selection method is applicable to various maize lines, based on co-transformation experiments where the expression of the second nonselected gene was used to assess stable sector frequency and size.

TABLE 2

Percentage of Plantlets Expressing GUS Activity After Germination on Nonlethal Selection Medium

| Experiment | N10000 | P10000 | W20000 | E10000 | PHP02 | R20000 |
|---|---|---|---|---|---|---|
| A | 65.6 | — | — | — | — | — |
| B | 23.1 | — | — | — | — | — |
| C | — | — | — | 16.7 | — | — |
| D | — | — | — | 71.1 | — | — |
| E | 00.0 | — | 38.5 | — | — | — |
| F | 16.4 | — | — | — | 7.3 | — |
| G | 12.3 | — | — | — | — | 20.0 |
| H | 39.1 | — | — | — | — | — |
| I | — | — | — | 20.0 | — | 15.5 |
| J | — | — | — | 7.2 | — | — |
| K | — | — | — | 4.3 | — | — |
| L | — | 5.0 | — | — | — | — |
| M | — | — | — | 5.0 | — | 1.3 |
| Averages | 26.1 | 5.0 | 38.5 | 20.7 | 7.3 | 12.3 |

(c) Evaluation of Transformation Frequency When Meristem Reorganization Is Effected by Mechanical Disruption of Apical Dome Prior to Bombardment Ears of genotypes E10000 and W20000 were harvested at the early coleoptilar stage of development and at 11 and 9 days, respectively, after pollination. One hundred and sixty embryos were isolated and incubated on maturation medium, as described above.

The apical dome of several embryos was disrupted prior to bombardment to force the meristem to reorganize and form new meristematic areas. Mechanical disruption was performed by means of micromanipulation needles, ranging from 0.5 μm to 5 μm in diameter, which were attached to a World Precision Instruments M3301 micromanipulator. Needle penetration of each embryo was effected in the center of the apical dome to a depth ranging from a few microns to a few hundred microns, depending on the morphology of the embryo (embryos with a larger scutellem will tolerate deeper penetration). The preferred targeted depth of penetration was between 50 μm and 150 μm. Embryos then were bombarded with NPTII and GUS constructs, as described above.

Embryos were maintained in the dark at 28° C. for seven days on Maturation Medium and then transferred to 272K medium containing 150 mg/L Tobramycin sulfate. At time of transfer, embryos had multiple meristem formation with elongated cotyledons. Embryos were incubated in the light at 28° C.

At two, three and four weeks post-bombardment, first and second leaves of recovered plantlets were analyzed for GUS expression by histochemical assay. Table 3 shows the results of GUS assays, as well as observations on meristem formation.

TABLE 3

Effect of Mechanical Disruption on Transformation Efficiency and Meristem Formation

| Manipulation | N | # New Meristems | % GUS-Positive Plants |
|---|---|---|---|
| 150 μM | 80 | 89 | 45.9% [17/37 analyzed] |
| none | 60 | 0 | 37.5% [3/8 analyzed] |

These data demonstrate that the mechanical disruption of the apical dome resulted in new meristem formation and a higher frequency of transformation. In addition, mechanical disruption provided a more continuous GUS expression pattern in relation to non-manipulated plants, which displayed a narrower, more spotty pattern of GUS expression. Thus, meristems not disrupted frequently exhibited leaf tip GUS expression only, whereas most of the meristems that were disrupted showed wide, continuous sectors in leaves.

EXAMPLE 2

Transformation with Shoot Multiplication (A) General Methodology

Embryos at the coleoptilar stage were isolated and cultured scutellum side down on an embryo maturation medium (10–20 embryos/plate). Since there can be considerable seasonal and genotypic variation affecting embryo ontogeny, embryo stage rather than size or days after pollination, was monitored carefully.

Embryos typically were matured on MS-based medium containing 0.5 mg/L zeatin, 1 mg/L indoleacetic acid, and elevated sugar levels which serve as an osmoticum. The embryos were cultured for a period ranging from 0–48 hours post-isolation, with 12–24 hours being optimal. Meristems then were bombarded with genes conferring kanamycin or streptomycin resistance, along with other nonselected genes, such as agronomic or visual marker genes.

After bombardment, the embryos were cultured in the dark to promote germination. After one to two weeks, the embryos were moved to a germination medium, such as hormone-free or low-hormone MS medium. The germinated plantlets generally had a swelling at the junction between the mesocotyl and epicotyl. This swelling occurred in the region containing the developing shoot meristem.

Two to three millimeter sections including the meristem were excised and cultured on a shoot proliferation medium which contained the appropriate hormones and a selection agent. The sections were regularly trimmed of elongated leaves and transferred to fresh medium every 10 to 14 days. Cultured meristems were incubated at 28° C. in the dark. After three to nine weeks, the proliferating meristems were transferred to an illuminated culture room.

Transformed sectors were identified one to two weeks after culture in the light, based on their green phenotype, i.e., nontransformed tissue remained bleached upon selection. In general, plants were regenerated by lowering the hormone concentration, although in some genotypes cytokinin concentrations were increased to promote plant regeneration. Since regenerated plants sometimes have difficulty rooting, rooting was promoted by culture on SH medium with 1 mg/l NAA, or by nicking the base of the stem and dipping the shoots in a 1 mg/ml NAA solution.

(B) NPTII Transformation of Honey and Pearl

One hundred eighty coleoptilar-stage maize embryos of the Honey and Pearl variety were harvested nine days after pollination. The scutella of the isolated embryos averaged 0.48 mm in length. These embryos were placed on embryo Maturation Medium (10 embryos per plate) and cultured overnight in the dark at 28° C.

Sixteen plates of the embryos were bombarded twice according to the above-described method with plasmid DP551, using 1.8 µm tungsten particles at a DNA concentration of 10 µg DNA/tube of tungsten. Plasmid DP551 contains ADH intron 1, GUS gene, and nos terminator, as well as ADH intron 1, NPTII gene, PinII terminator. Both GUS and NPTII genes are regulated by 35S CaMV sequences. Plates containing these embryos were cultured and matured in the dark at 28° C. Eight days later, a few of the embryos were placed in X-Gluc histochemical stain. All embryos contained intense blue staining, indicating GUS activity.

Most of the embryos had germinated nineteen days after particle bombardment. At this time, the region containing the meristem and leaf primordia was excised as described above and cultured on agar solidified MS medium with 2 mg/L BAP and 50 mg/L kanamycin. Leaf tissue was stained and chimeric blue staining sectors were observed in eight of the sixteen plates. The region containing the meristem was trimmed of elongated leaves and transferred to fresh medium every 10 to 14 days. Twenty six days after bombardment, the level of kanamycin was increased to 100 mg/L. Proliferating meristems were transferred to the light a week later. These experiments produced three independent transformation events. Two of the transformants have been characterized by PCR, GUS staining, NPTII ELISA assay and Southern analysis. One of these events exhibited strong GUS activity and high levels of NPTII protein. The T1 and T2 generations from this event were used for subsequent analysis. Progeny displayed a co-segregating, 1-to-1 ratio after outcrossing, based on both GUS activity and NPTII ELISA results (see Table 4) consistent with Mendelian inheritance of the integrated genes. Integration and segregation of the NPTII gene, which correlated with positive NPTII ELISA results, were demonstrated through Southern analysis of $T_1$ plants.

(C) aadA Transformation of Honey and Pearl

Coleoptilar stage Honey and Pearl embryos were isolated and cultured on 288B medium (MS medium with 0.5 mg/l zeatin, 1mg/l IAA, 0.25M sorbitol, and 4% sucrose solidified with 3 g/l gelrite). Eight plates with ten embryos per plate were bombarded once, as described above. Each particle preparation (enough for six shots) employed a combined total of 10 µg of DNA (5 µg DP4790+5 µg DP460 or DP3536). Plates 1 to 4 were bombarded with plasmid DP4790, which contains a 35S CaMV promoter, omega', aadA and ocs terminator (provided by Dr. Jonathan Jones, John Innes Institute), and with plasmid DP460, which contains a 35S CaMV promoter, ADH intron, GUS gene, and nos terminator. Plates 5 to 8 were bombarded with plasmids DP4790 and DP3536. The latter plasmid contains a cab promoter, ADH intron 6, GUS gene, and ocs terminator. All embryos were grown and germinated as described in part (B) of this example, supra. After germination, the regions containing the meristems were cultured on agar-solidified MS medium containing 2 mg/L BAP and 100 mg/L streptomycin sulfate.

After cultured meristems were moved to an illuminated culture room, a green sector was observed on a proliferating meristem on plate 6. All other cultured meristems were white due to streptomycin bleaching. GUS staining at this time revealed a mix of sectored and non-sectored blue staining leaves. About seven weeks after bombardment, sorting out was observed in the leaves from the transformation event on plate six. Some leaves were non-sectored GUS+ while others were still mericlinal. Transformation was confirmed using PCR, GUS staining and Southern analysis.

(D) Transformation of an Elite Inbred

Eight days after pollination, coleoptilar stage embryos of an elite inbred, designated "B30000" for purposes of this description, were isolated and cultured on 288L medium in fifteen plates containing twenty embryos per plate. Twelve plates were bombarded, using standard protocols. Briefly, particle bombardment was performed with six shots using 650 psi rupture disks and 1 µm tungsten particles, which were coated with plasmids DP5397 (proprietary agronomic gene) and DP5606 (Ubi promoter/Ubi-intron/NPTII/pin II terminator linked to cab promoter/ADH intron 6/GUS/ocs terminator) at a concentration of 5 µg DNA/particle preparation tube for each plasmid.

Plasmid DP5397 is a proprietary agronomic plasmid which contains a Bt gene, while plasmid DP5606 contains the Ubi promoter, Ubi intron, NPTII gene, and PinII terminator, which is linked to a cab promoter, ADH intron 6, GUS gene, and ocs terminator.

After bombardment the meristems were cultured on agar solidified MS medium containing 2 mg/L BAP, 0.25 mg/L, 2,4-dichlorophenoxy acetic acid and 3% sucrose. Five weeks after bombardment, meristems were placed on kanamycin selection (100 mg/L). To avoid irreversible bleaching of the meristems, this tissue was cycled between selective and non-selective media.

Five months after bombardment, a large green sector was removed from a bleached shoot culture. Three small leaves were removed from the sector and stained with X-Gluc. The leaves were found to express GUS activity in non-epidermal cells.

A single plant was regenerated from this series of experiments. The plant produced copious amounts of pollen and several ears. The pollen was found to be segregating for GUS expression, which was surprising since this gene was under the control of the cab promoter. All leaves of this plant exhibited strong, non-sectored GUS activity. The tassel glumes also were positive for GUS activity. Samples of leaf tissue from this $T_0$ plant contained the NPT-II and Bt proteins (as verified by their respective ELISA's) and exhibited strong GUS activity (fluorometric analysis). The GUS histochemical assay verified transmission to progeny in 42 of 106 seedlings sampled to date, which is consistent with Mendelian inheritance.

EXAMPLE 3

Transformation Regimen Employing Immature Ear and Tassel Meristems (A) Excision of Immature Ears From plants harvested seven to nine weeks after planting, leaves were removed aseptically, one at a time, and the ears were exposed. The ears were dissected out of the husks under a dissecting microscope. Longitudinal bisection of the ears increased the response and exposed the meristems more fully to bombardment.

(B) Staging and Selection of Responsive Explants

The size of the whole excised ear and the developmental stage of the meristems were found to be reliable indicators of proper timing of harvest. Smaller ears are less developmentally determined and more responsive to hormonal stimuli, but fewer meristems survive resulting in fewer targets for transformation. Although smaller inflorescences have been used, two millimeters was used as the practical lower size limit for transformation experiments. The upper limit for selection of responsive targets was determined by meristem stage; developmental plasticity decreased dramatically once the glumes began to be obvious and approached the sides of the meristematic dome.

(C) Initial Culture Medium

Various media have been used, and inbreds respond differently to these variations. A preferred medium used in the initial stage of floral meristem culture (used for various genotypes) consisted of Murashige and Skoog salts, MS vitamins, 0.1 mg/l 2,4-D, 0.5 gm/l 6-BAP, l-proline at 12.2 µM, 8% sucrose, and silver nitrate at 30 mg/l. A preferred gelling agent is GELRITE (product of Merck and Co, Inc./Kelco division, Rahway, N.J.) at 3.5 g/l.

(D) Bombardment

Immature ear explants were bombarded using 650 psi rupture disks and a stainless steel screen (100 um mesh size) suspended approximately 0.5 to 1.0 cm above the tissue. DNA precipitation and other bombardment parameters were as described in Example 1.

(E) Subsection, Subculture and Selection

Maintenance of rapid growth and survival of individual meristems was achieved by subsecting the ears four to six days after isolation, into pieces with four to eight meristems each. These pieces were cultured onto shoot multiplication medium, which has the same basal composition as the initial culture medium (above) but with 1 mg/l BAP and 3% sucrose. Meristem tissue was subcultured repeatedly, at two week intervals on the shoot multiplication medium.

Incubation of bombarded ear meristems in X-gluc consistently resulted in high frequencies of transient GUS expression two days after bombardment. Stable sectors in leaves produced by multiple shoot clumps were found to express GUS one month after bombardment, At this stage, leaves were approximately 1 to 2 cm in length, and transformed sectors were found that extended more than half the length of the leaf. In addition, one meristem sacrificed at this stage expressed high levels of GUS in a histochemical assay.

One month of shoot multiplication was followed by one month of selection using 100 mg/l streptomycin. After this treatment, all material was subcultured once more onto medium without the selective agent, and were additionally moved into the light. Leaves and shoots in non-selected cultures quickly turned green. Leaves in selected cultures remained bleached (white).

(F) Plant Regeneration

Putatively transformed shoots clumps were transferred to medium lacking plant growth regulators. Varying degrees of leaf development occurred on 1 mg/l BAP, and shoots soon formed and elongated in the absence of hormones.

(G) Rooting

Rooting at high frequency was effected via several days of exposure to MS- or SH-based media with 1–5 mg/l NAA.

EXAMPLE 4

Transformation of Early Proembryo, Mid Proembryo, Late Proembryo, Transitional and Early Coleoptilar-Stage Embryos Immature embryos at the mid proembryo, late proembryo, transitional and early coleoptilar stage were harvested and cultured on culture medium 610A, containing high concentrations of cytokinin and osmoticum. The 610A culture medium comprised MS salts, MS vitamins, 100 mg/L myo-inositol, 0.4 mg/L thiamine-HCl, 1 mg/L zeatin riboside, 0.1 mg/L BAP, 60 g/L sucrose, 400 mg/L asparagine, and 7 g/L Hazelton TC agar. After one day of recovery, the embryos were bombarded with DNA, by means of the particle gun as described above, and punctured in the center of the area of where the apical meristem will develop with a 0.5 µm micromanipulation needle.

Embryos were allowed to mature for 7 days in the dark and then transferred to a hormone-free medium containing 1 mg/l bialaphos. Following another 7 days of culture on hormone-free medium in the dark, the embryos were transferred to germination medium, and cultured in the light for continued germination. As leaves developed, plant phenotype was observed and samples were taken to check for sector formation by histochemical assay (GUS) as described above.

Healthy plants with normal phenotype and/or reporter gene activity were transferred to the greenhouse for maturation. The data shown in Table 4, which were generated via the above-discussed protocol, demonstrate for inbred N10000 the sector frequency obtained across several similar experiments, using embryos staged at mid proembryo, late proembryo, transitional, and early coleoptilar.

TABLE 4

Sector Frequency Obtained With Mid Proembryo, Later Proembryo, Transitional and Early Coleoptilar Stage Embryos

| Embryo Stage | N | Transgenes | GUS frequency | GUS pattern of expression | Sector Placement |
|---|---|---|---|---|---|
| Early Coleoptilar | 328 | BAR/GUS | 14.2% | Leaf tips and files of 1–3 cells | Leaves 1 and 2 |
| Transitional | 250 | BAR/GUS | 22.5% | Saddle and Linear | Sectors start at Leaf 1, 5 or 11 |
| Late Proembryo | 200 | BAR/GUS | 34% | Saddle and Linear | Sectors start at Leaf 1 or Leaf 5 |
| Mid Proembryo | 110 | BAR/GUS | 3% | Linear and whole leaf | Sectors start at Leaf 1 |

The GUS frequency observed after targeting mid proembryos reflected, at the time these data were collected, a relatively poor survivial rate after bombardment and selection. But the addition of 1 mg/l zeatin to medium 610A, an increasing of the agar concentration (12 g/l), and the use of lower rupture disc pressure (200 p.s.i.) during particle delivery increases survival of mid proembryos after isolation and DNA delivery.

EXAMPLE 5

Meristem Transformation—Direct Germination Approach

Genotype N10000 plants were pollinated and, eight days later, embryos were placed into culture. The harvested embryos thus were late-proembryo stage.

More specifically, embryos were cultured at day 0, axis up, onto modified 610A medium, containing 150 g/l sucrose, 1 mg/l zatin, and 12 g/l agar, and incubated at 28° C. overnight in the dark. At day 1, following the overnight incubation, the apical meristems of all embryos were disrupted in the center of the apical dome using a 0.5 µm Femtotip micromanipulation needle. All embryos were returned for an overnight incubation at 28° C. in the dark. At day 2 bombardment was effected with the PDS-1000 Helium particle gun, one shot per plate, using 650PSI rupture disks. DNA employed in this regard was DP3528+DP3953 [2×35S::BAR+UBI::GUS] at 1 µg/tube of 1-µm tungsten. At day 2 all embryos were maintained in the dark at 28° C. for 7 days on 610A medium to allow meristem maturation to occur. At day 7 (after 7 days on 610A), embryos were transferred to 612 medium containing MS salts and vitamins, 0.001 mg/l kinetin, 0.1 mg/l adenine sulfate, 20 g/l sucrose, 6 g/l agar and 0.5 mg/L bialaphos, for germination and selection. At day 14 embryos were kept in the dark at 28° C. for 7 days before transfer to the light for further germination. On days 21–49 GUS histochemical assays on developing leaves were conducted, and on day 35 growing plantlets were transferred to tubes containing MS medium with no hormones and 5 mg/L bialaphos. On day 56 plant 6-1 (SID 180741) and plant 2-7 (SID 180742) were transferred to the greenhouse.

The total number of embryos cultured and bombarded was 48, of which 37 developed normally. The number of embryos that grew beyond leaf 1 was 17, with four plants showing GUS expression. Two plants survived 5 mg/L-bialaphos selection with normal root development, and were transferred to the greenhouse for maturation.

SID 180741 and 180742 both showed GUS expression at the time of greenhouse transfer and had normal leaf and root development, whereas all other plants died. SID 180742 showed GUS expression in leaves 1–8 only.

TABLE 5

Sector Placement by GUS histochemical assay of SID180741

| Structure | GUS phenotype |
| --- | --- |
| Leaf 1 | negative |
| Leaf 2 | leaf tip |
| Leaf 3 | leaf tip |
| Leaf 4 | saddle sector: margin and midrib |
| Leaf 5 | midrib sector |
| Leaf 6 | saddle sector margin and midrib |
| Leaf 7 | midrib sector |
| Leaf 8 | saddle sector margin and midrib |
| Leaf 9 | midrib sector |
| Leaf 10 | saddle sector margin and midrib |

TABLE 5-continued

Sector Placement by GUS histochemical assay of SID180741

| Structure | GUS phenotype |
| --- | --- |
| Leaf 11 | midrib sector |
| Leaf 12 | saddle sector margin and midrib |
| Leaf 13 | midrib sector |
| Leaf 14 | half leaf |
| Leaf 15 | half leaf |
| Leaf 16 | half leaf |
| Leaf 17 | half leaf |
| Leaf 18 | half leaf |
| Leaf 19 | half leaf |
| Leaf 20 | entire leaf |
| Leaf 21 | entire leaf |
| Tassel | To date: central stalk shows pollen staining; 5 tassel branches also positive |
| Anthers | Endothecium and epidermis positive |
| Anther glumes | Epidermis positive |

Leaves were painted with 1% Ignite in lanolin paste at the V6–V8 stage of development. SID 180741 showed resistance to Ignite in the sectored (GUS expressing) areas only. SID 180742 showed no resistance to Ignite. PCR analyses were done on sampled leaves and confirmed presence of both GUS and BAR genes in SID 180741 and GUS genes in SID 180742.

One of the first major differences observed after moving towards an earlier developmental stage, i.e., when targeting late proembryos, was the production of saddle sectors (see Poethig (1986), supra, for a description). Extant information concerning meristem organization suggested to the present inventors that this might lead to germline transmission through the tassel. Saddle sectors extend from the leaf primordium up through the central portion of the apical dome and back into another portion of the leaf primordium. The extension of transgenic sectors into the central portion of the meristem greatly increases the probability of the sector contributing to the tassel and, ultimately, to pollen.

Previous research on maize anatomy and clonal analysis has shown that maize contains an organized, layered apical meristem beginning at the transitional stage of development. See Randolph, J. Agric. Res. 53: 881–916 (1936), and Poethig (1986), supra. Furthermore, a paper by Dawe and Freeling, Developmental Biol. 142: 233–45 (1990), regarding cell lineages in the male flower of maize, indicated that the L1 and L2 layers of the apical meristem give rise to the two layers of the anther wall. Only the inner layer is derived from the same cell lineage as the male germ cells, the L2. It also was found that events that occurred (by irradiation) before the organization of the shoot apical meristem contained sectors in both layers of the anther wall with inheritance through the pollen. Events that occurred after the transitional stage of development were limited to only one cell lineage with inheritance only when sectors occurred in the L2 layer.

Transformant 180741 was bombarded by the particle gun at the late proembryo stage of development, before meristem layer organization occurs. It contained a saddle sector which, by definition, is a sector which traverses the apical dome and bisects the meristem, in a region of the meristem that will later develop into the tassel (see Poethig (1986), supra). It also was wounded by a micro-manipulation needle, to encourage meristem reorganization, and exposed to bialaphos as the selective agent. GUS histochemical data showed expression in both layers of the leaves, in the anther wall, and in about 50% of the pollen from the central stalk.

EXAMPLE 6

Stabilization of Transgenic Sectors by Means of Tillering

As noted above, tillering of transformed plants is an alternative to shoot multiplication for stabilization of transgenic sectors. Accordingly, elite lines may be induced to tiller, pursuant to the present invention, thereby stabilizing transgenic sectors.

In this example, tillering was induced in control plants using the method described by De Wolff, *Euphytica* 20: 524–26 (1971). A triangular incision was made with a number 11 scalpel blade at the approximate height of, or slightly above, the shoot apex of two week-old seedlings. The incision was made perpendicular to the plane of the leaves in order to avoid damage to the midribs. The shoot apex was removed from P10000, PHP02, G30000 and EI0000 seedlings. Each of these genotypes represents inbreds from significantly different heterotic families. Untreated plants of the same genotype were used as controls. If the incision was too far above the apex the procedure was repeated just below the initial incision.

The wounded plants and untreated controls were maintained in 24 hour continuous light (greenhouse during the day, growth chamber by night) for two weeks. A replicate treatment was grown under light/dark conditions.

Significant tillering was observed in the plants from which apices were removed. The influence of continuous light on tillering frequency, relative to normal light/dark conditions, was variable and may depend on genotype. The untreated controls did not tiller.

The hole made by the incision could have been plugged with lanolin and phytohormones, such as TIBA (1 mg/L) or BAP (10 mg/L), to increase tillering frequency. In the alternative, or in addition to the phytohormones, selective agents such as kanamycin could have been added to the incision to identify and select transgenic sectors.

What is claimed is:

1. A method for producing transgenic cereal plants that will transmit introduced DNA to progeny, comprising the steps of
   (A) introducing foreign DNA into target cells selected from the group consisting of (i) cells of a meristem that is not enclosed by primordial sheathing leaves and (ii) cells that contribute to said meristem; then
   (B) inducing reorganization of said meristem to increase transgenic sector size, whereby the likelihood that a transgenic sector will contribute to germline transmission is increased, wherein said reorganization is effected through at least one manipulation selected from the group consisting of (i) imposition of a nonlethal selective pressure on said meristem, (ii) mechanically-induced meristem reorganization, and (iii) hormonally-induced shoot multiplication combined with nonlethal selective pressure; and thereafter
   (C) exposing said meristem to conditions under which it differentiates to form a plantlet, wherein said plantlet contains said transgenic sector or is homogeneously transformed by said foreign DNA, such that said plantlet can be grown into a transformed cereal plant that will transmit said foreign DNA to progeny.

2. A method according to claim 1, wherein step (A) is effected at early proembryo, mid proembryo, late proembryo, transitional or early coleoptilar stage.

3. A method according to claim 1, wherein said foreign DNA is introduced into a plurality of meristems, and at least some of said meristems differentiate in step (C) to form a plurality of plantlets.

4. A method according to claim 1, wherein said conditions in step (C) are such that said meristems undergo maturation and plant differentiation to form shoot apices, and wherein said method further comprises effecting reorganization of meristem tissue in said shoot apices to enlarge transformed sectors or to produce periclinal L2 chimeras.

5. A method according to claim 4, wherein said effecting of reorganization comprises exposing said shoot apices to nonlethal selection pressure such that transformed cells have a competitive growth advantage over nontransformed cells in said shoot apices, and the proportion of transformed cells in said shoot apices is increased.

6. A method according to claim 1, where step (A) comprises biolistic bombardment of an embryo at a developmental stage no later than the coleoptilar stage.

7. A method according to claim 4, wherein said effecting of reorganization comprises culturing said shoot apices under conditions such that multiple shoots proliferate therefrom through organogenesis.

8. A method according to claim 1, further comprising a step before step (C) of wounding said apical dome selectively.

9. A method according to claim 8, wherein said wounding is carried out before step (A).

10. A method according to claim 1, wherein step (A) comprises biolistic bombardment of meristems on immature ear or tassel explants.

11. A method according to claim 1, wherein said target cells are maize, sorghum, wheat, barley, oat or rice target cells.

12. A method according to claim 11, wherein said target cells are maize target cells.

13. A method according to claim 4, further comprising the steps of (i) dissecting out of an axillary bud from above the base of a leaf of a plantlet when a chimeric sector is observed in a substantial portion of said leaf, and then (ii) germinating said axillary bud into a whole plant or subjecting said axillary bud to shoot multiplication.

14. A method according to claim 1, further comprising the steps of (i) removing the shoot apex from seedlings of said plantlet, whereby a wound is produced, then (ii) growing said plantlets to induce formation of a plurality of tillers, and (iii) selecting a transgenic tiller from said plurality.

15. A method according to claim 14, wherein phytohormones that increase tillering are introduced, subsequent to step (i), into said wound.

16. A method according to claim 14, wherein a selective agent is introduced after step (i) into the wound, to identify and select transgenic sectors.

17. A method according to claim 1, wherein said nonlethal selective pressure is provided by a selective agent selected from the group consisting of kanamycin, streptomycin, hygromycin, norflurazon and bialaphos.

* * * * *